(12) United States Patent
Robinson et al.

(10) Patent No.: US 7,556,796 B2
(45) Date of Patent: Jul. 7, 2009

(54) DIRECTED COMPLEMENTATION

(75) Inventors: Murray Robinson, Boston, MA (US);
Ronan O'Hagan, Brookline, MA (US);
Karuppiah Kannan, Cambridge, MA (US); Ti Cai, Andover, MA (US); Maria Isabel Chiu, Newton Centre, MA (US);
Lorena Lerner, Newton Centre, MA (US); Jie Lin, West Roxbury, MA (US);
Yinghui Zhou, Belmont, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 83 days.

(21) Appl. No.: 11/398,171

(22) Filed: Apr. 5, 2006

(65) Prior Publication Data

US 2006/0228302 A1    Oct. 12, 2006

Related U.S. Application Data

(63) Continuation-in-part of application No. 11/282,847, filed on Nov. 17, 2005, now abandoned, which is a continuation-in-part of application No. 11/099,735, filed on Apr. 5, 2005, now abandoned.

(51) Int. Cl.
*A61K 49/00* (2006.01)
*A61K 35/12* (2006.01)

(52) U.S. Cl. .................... 424/9.1; 424/520; 424/573

(58) Field of Classification Search .................. None
See application file for complete search history.

(56) References Cited

U.S. PATENT DOCUMENTS

| | | | |
|---|---|---|---|
| 6,639,121 | B1 | 10/2003 | DePinho et al. |
| 2006/0222589 | A1 | 10/2006 | Robinson et al. |
| 2006/0222590 | A1 | 10/2006 | Robinson et al. |

FOREIGN PATENT DOCUMENTS

| WO | WO-01/09308 | 2/2001 |
|---|---|---|
| WO | WO-02/079419 | 10/2002 |
| WO | WO-2004/058948 | 7/2004 |
| WO | WO-2004/089073 | 10/2004 |
| WO | WO-2005/020683 | 3/2005 |

OTHER PUBLICATIONS

Cooper (Oncogenes, 2nd Ed., 1995, p. 4).*
Allen et al., "Complementation Tagging of Cooperating Oncogenes in Knockout Mice" Seminars in Cancer Biology, vol. 7, 1996, 299-306.
Chin et al., "Essential Role for Oncogenic Ras in Tumour Maintenance," 1999 Nature, vol. 400:468-472.
Ding et al., "Mouse Astrocytoma Models: Embryonic Stem Cell Mediated Transgenesis," Journal of Neuro-Oncology, vol. 53, No. 3, Jul. 2001, pp. 289-296.
International Search Report for PCT/US2006/012965, dated Aug. 3, 2006.

* cited by examiner

*Primary Examiner*—Karen A Canella
(74) *Attorney, Agent, or Firm*—Gary L. Creason

(57) ABSTRACT

A method of producing a tumorigenic mouse cell, the tumorigenicity of which depends on a recombinant gene of interest is disclosed. The method involves: (a) providing a conditionally tumorigenic mouse cell containing a recombinant oncogene operably linked to an inducible promoter, wherein (i) expression of the recombinant oncogene is necessary and sufficient for the tumorigenicity of the tumorigenic mouse cell, and (ii) the inducible promoter is in the uninduced state; and (b) introducing into the cell a recombinant gene of interest that functionally complements the oncogene, thereby restoring tumorigenicity without expression of the inducible recombinant oncogene. Also disclosed is a method of testing a compound for anti-tumor effects. The method includes producing tumorigenic mouse cells the tumorigenicity depends on expression of a recombinant gene of interest, implanting the cells in mice and obtaining tumors from the implanted cells, administering test compounds to the mice, and determining anti-tumor effects, if any, of the compounds.

12 Claims, 9 Drawing Sheets

| DC Tumor Description | Tumor name | Human HGF ng/mg protein | ST DEV |
|---|---|---|---|
| DC: (Met/HGF)-T3 | 4268 | 77.09 | 0.47 |
| propagated X1 (Met/HGF)-T3 | 4268x# | 23.50 | 1.07 |
| propagated X1 (Met/HGF)-T3 | 4268x#3 | 51.77 | 1.60 |
| propagated X1 (Met/HGF)-T3 | 4268x#5 | 40.26 | 5.48 |
| DC: (Met/HGF)-T7 | 4272 | 19.99 | 0.83 |
| propagated X1 (Met/HGF)-T7 | 4272x#3 | 10.95 | 0.48 |
| propagated X1 (Met/HGF)-T7 | 4272x#4 | 15.49 | 0.41 |
| propagated X1 (Met/HGF)-T7 | 4272x#5 | 8.35 | 0.57 |
| DC: (Met/HGF)-T3' | 4275 | 5.79 | 0.15 |
| propagated X1 (Met/HGF)-T3' | 4275x#1 | 5.93 | 0.16 |
| propagated X1 (Met/HGF)-T3' | 4275x#3 | 20.79 | 0.70 |
| propagated X1 (Met/HGF)-T3' | 4275x#4 | 6.46 | 0.69 |

FIG. 7

DIRECTED COMPLEMENTATION

RELATED APPLICATIONS

This application claims priority from U.S. application Ser. No. 11/099,735, filed Apr. 5, 2005 and Ser. No. 11/282,847, filed Nov. 17, 2005.

FIELD OF THE INVENTION

The field of the invention is molecular biology, oncology and drug development.

BACKGROUND OF THE INVENTION

Mouse models of cancer in which primary tumors are driven by specifically engineered oncogenes have been increasingly useful tools in cancer research in recent years. Although they require relatively long timeframes for genetic crosses and latency of spontaneous tumors, current methods of producing such genetically engineered mice generally have been adequate for producing relatively small numbers of genotypes for basic research.

Primary tumors from mouse models would be particularly useful in drug development studies, as well as in basic research. This is because similar or indistinguishable tumor phenotypes, e.g., breast carcinoma, can undergo neoplastic transformation through the spontaneous acquisition of different mutations, which leads to different tumor cell genotypes. Due to the different genotypes of different tumors, a given drug may be efficacious against one tumor but not against the another tumor of the same phenotype. Consequently, conventional xenograft experiments using an established human cancer cell line are likely to provide an incomplete picture. For the same reason, clinical trial data simply will indicate that the drug is effective in some patients but not others.

In spite of the desirability of genetically defined primary tumor material for drug development studies, the time and resources that would be required to generate the necessary mouse models have made it impractical to design preclinical drug development studies around the use of primary tumor material in which tumorigenicity depends on a pre-selected gene of interest, i.e., target gene.

SUMMARY OF THE INVENTION

The invention provides an efficient method for generating a tumorigenic mouse cell, i.e., primary tumor material, the tumorigenicity of which depends on a recombinant gene of interest. The method includes (a) providing a conditionally tumorigenic mouse cell containing (i) a tumor suppressor knockout, and (ii) a recombinant oncogene operably linked to an inducible promoter, wherein (1) expression of the recombinant oncogene is necessary and sufficient for tumorigenicity of the conditionally tumorigenic mouse cell, and (2) the inducible promoter is in the uninduced state; and (b) introducing into the cell a recombinant gene of interest that functionally complements the oncogene, thereby restoring tumorigenicity without expression of the inducible recombinant oncogene.

Examples of tumor suppressor genes that can be usefully knocked out are Rb, P53, INK4a, PTEN, LATS, Apaf1, Caspase 8, APC, DPC4, KLF6, GSTP1, ELAC2/HPC2, NKX3.1, ATM, CHK2, ATR, BRCA1, BRCA2, MSH2, MSH6, PMS2, Ku70, Ku80, DNA/PK, XRCC4, Neurofibromatosis Type 1, Neurofibromatosis Type 2, Adenomatous Polyposis Coli, the Wilms tumor-suppressor protein, Patched and FHIT. Tumor suppressor genes preferably knocked out are INK4a, P53, PTEN and Rb. Knock out of INK4a is particularly preferred.

Examples of recombinant oncogenes useful in the present invention include Her2, KRAS, HRAS, NRAS, EGFR, MDM2, TGF-β, RhoC, AKT, c-myc, β-catenin, PDGF, C-MET, PI3K-110α, CDK4, cyclin B1, cyclin D1, estrogen receptor gene, progesterone receptor gene, ErbB1, ErbB3, PLK3, KIRREL, ErbB4, TGFα, ras-GAP, Shc, Nck, Src, Yes, Fyn, Wnt, Bcl2, PyV MT antigen, and SV40 T antigen. Preferred oncogenes are Her2, C-MET, PI3K-CA and AKT. Her2 and KRas are particularly preferred.

Examples of suitable inducible promoter systems to control expression of the recombinant oncogene include a tetracycline-dependent promoter regulatory system, a metallothionine promoter system, an IPTG/lacI promoter system, an ecdysone promoter system, and a Gal4/UAS system.

The invention also includes a method of testing a compound for anti-tumor effects. The method includes the steps of: (a) producing, as described above, a multiplicity of tumorigenic mouse cells, the tumorigenicity of which depends on expression of a recombinant gene of interest; (b) implanting the cells into a multiplicity of host mice; (c) obtaining tumors in the mice derived from the implanted cells; (d) administering suitable amounts of a test compound to the mice; and (e) determining anti-tumor effects, if any, of the test compound.

As used herein, "tumor suppressor knockout" means one or more mutations such that both alleles of an endogenous tumor suppressor gene are absent or nonfunctional.

Unless otherwise defined, all technical and scientific terms used herein have the same meaning as commonly understood by one of ordinary skill in the art to which the invention pertains. In case of conflict, the present specification, including definitions, will control. All publications, patents and other references mentioned herein are incorporated by reference in their entirety.

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

BRIEF DESCRIPTION OF THE DRAWINGS

FIG. 7 is a table summarizing the hHGF capture ELISA results on hMET/hHGF-DC tumors. Whole-cell lysates were prepared from hMET/hHGF DC tumors and their propagated counterparts. The levels of hHGF were measured by ELISA against a standard curve prepared with recombinant pure hHGF protein.

DETAILED DESCRIPTION OF THE INVENTION

The present invention provides a practical method for efficiently obtaining a tumorigenic mouse cell, the tumorigenicity of which depends on a recombinant gene of interest. Without intending to be bound by theory, the inventors note that in general, neoplastic transformation results from an accumulation of mutations, rather than a single mutation. Therefore, merely transfecting a wild type mouse cell, e.g., a mammary epithelial cell, with a recombinant oncogene of interest would not be sufficient to yield a tumorigenic cell.

To address this issue, a mouse can be engineered to express a recombinant oncogene in a tissue-specific or organ-specific manner, in the target tissue or organ, and to lack expression of a tumor repressor gene. See, e.g., U.S. Pat. No. 6,639,121; and WO 2005/020683. Following a latency period during which mutations accumulate, tumors arise spontaneously in the target tissue or organ.

Figure 1:
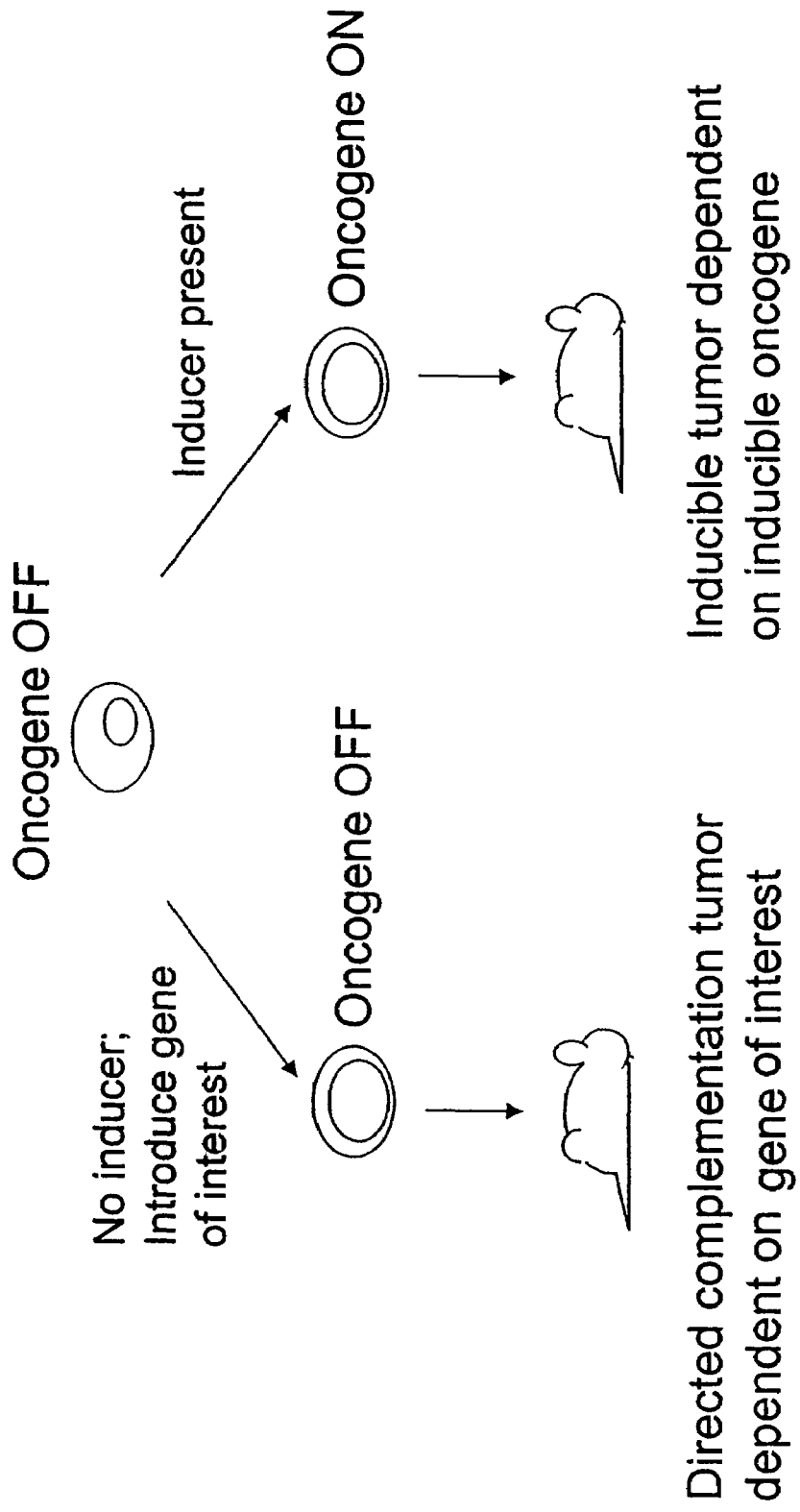
FIG. 1 is a schematic drawing of illustrating the basic concept of directed complementation.

These spontaneous tumors are generally dependent upon expression of the inducible recombinant oncogene. When the inducer is withheld from the animal, the tumor regresses, and the cells of the target tissue or organ become non-tumorigenic. However, the cells of the target tissue or organ are only one mutation away from being tumorigenic. All that is necessary to restore tumorigenicity is: (1) expression of the inducible recombinant oncogene, or (2) expression of a gene that functionally complements the recombinant oncogene (FIG. 1).

For purposes of the present invention, the cells at this point are said to be "conditionally tumorigenic cells." A nucleic acid encoding the recombinant gene of interest that functionally complements the recombinant oncogene is introduced into the conditionally tumorigenic cell by any suitable method, as further discussed below. Thus, genetic complementation is achieved in a directed manner, so as to obtain a tumorigenic cell in which tumorigenicity is driven by a pre-selected gene of interest. Typically, the gene of interest is a potential therapeutic target for anti-cancer molecules in a drug development program.

A single source of conditionally tumorigenic cells, e.g., a single primary tumor, can be used to generate numerous lines of primary tumor material, with the tumorigenicity of each line being dependent on a different, pre-selected, cancer-related gene of interest. A second source of conditionally tumorigenic mouse cells, dependent on a second oncogene, can be used to generate additional lines of primary tumor material, with the tumorigenicity of each line being dependent on a new set of pre-selected, cancer-related genes. A third source of conditionally tumorigenic mouse cells, dependent on a third oncogene, can be used, and so forth.

A notable advantage of the present invention is that when a single source of conditionally tumorigenic cells is used to generate different lines of primary tumor material by introducing different genes of interest, the effects of the different genes of interest on the tumors, with and without drug treatment, can be evaluated in exactly the same genetic background. In contrast, if separate mouse models were independently engineered to incorporate the same genes of interest and spontaneous tumors were generated, the genetic background of the gene of interest would be different in each model. Consequently, the type of comparison possible with the present invention would not be possible using the separately engineered models.

Looking at the genetic background question in the opposite way, a given gene of interest can be introduced separately into conditionally tumorigenic cells from multiple tumors. This will allow the effect of a given gene of interest, with and without drug treatment, to be evaluated in different genetic backgrounds.

For any given conditionally tumorigenic cell, the inducible recombinant oncogene is known. With knowledge of the inducible recombinant oncogene in hand, the skilled person can identity one or more genes of interest that will functionally complement the inducible recombinant oncogene. For example, the receptor tyrosine kinase, Her2/Neu/ErbB2 is known to be important for the viability of a subset of human breast cancers. Much is known about the downstream mediators of Her2, and this information has been summarized by publicly available sources, e.g., Biocarta. From such information, the skilled person can predict a useful number of complementing genes with a reasonable expectation of success. For example, genes expected to complement Her2 would include ErbB1/EGFR, ErbB3, PLK3, KIRREL, PI3K, Ras, Akt, Raf, Erk1 and Erk2.

One of the genes expected to complement Her2 is the ErbB3 gene, also known as HER3, MDA-BF-1 and MGC88033, which encodes a member of the epidermal growth factor receptor (EGFR) family of receptor tyrosine kinases. The ErbB3 membrane-bound protein has a neuregulin binding domain but not an active kinase domain. It therefore can bind the neuregulin ligand but not convey the signal into the cell through protein phosphorylation. However, it does form heterodimers with other EGF receptor family members which do have kinase activity. Heterodimerization leads to the activation of pathways which lead to cell proliferation or differentiation. Amplification of this gene and/or overexpression of its protein have been reported in numerous cancers, including prostate, bladder, and breast tumors (see, e.g., van der Horst et al., 2005, *Int J Cancer* 115:519-527; Holbro et al., 2003, *Proc Natl Acad Sci USA*. 100:8933-8938).

Another gene expected to complement Her2 is the gene designated PLK3 (polo-like kinase 3), also known as CNK, FNK, PRK, and 1_44702099GP201. The PLK3 gene encodes a putative serine/threonine kinase and is a member of the "polo" family of serine/threonine kinases, which is likely to play a role in cell cycle progression and tumorigenesis (see, e.g., Li et al., 1996, *J Biol Chem* 271:19402-19408). High expression of PLK3 has been detected in cancers of the bladder, breast, colon, ovary, pancreas and lung (see, e.g., Dai et al., 2000, *Genes Chromosomes Cancer* 27:332-336; Li et al., 1996, *J Biol Chem* 271:19402-19408).

Another gene expected to complement Her2 is the gene designated KIRREL, also known as NEPH1, FLJ10845, LOC348416 or 1_154843723-, which encodes a protein member of the nephrin-like protein family and contains an immunoglobulin domain. KIRREL expression is elevated in chondrosarcoma, glioblastomas, including glioblatomas expressing mutant activated EGFR, astrocytomas and medulloblastomas, pancreatic adenocarcinoma, breast carcinomas and colon adenocarcinoma, and melanomas.

Another gene known to be involved in tumorigenesis is mTOR kinase. Genes expected to complement mTOR kinase would include PI3Kinase, Akt1, Rheb, and S6Kinase. Another gene known to be involved in tumorigenesis is KRas. Genes expected to complement KRas would include Raf, Mekk1, Mekk2, Erk1, Erk2 and Jnk1.

In some cases, the skilled person will identify the recombinant gene of interest first, and then work "backwards" to identify an oncogene that would be functionally complemented by the gene of interest, based on knowledge available to one of skill in the art regarding signal transduction pathways and biochemical pathways that operate in particular types of cancer. That oncogene would be chosen as the inducible recombinant oncogene to use in producing the conditionally tumorigenic cells.

The gene of interest introduced into the conditionally tumorigenic mouse cells can be a mouse gene. In some embodiments of the invention, however, it may be preferable to introduce the human ortholog of the gene of interest into the conditionally tumorigenic mouse cells. An advantage of employing the human gene is that when the resulting tumors are subsequently used in drug development studies, the test compounds will be tested against the human target molecules rather than the mouse orthologs. Working with the human molecules will eliminate one potential source of unpredictability relatively early in the drug development process.

The source of conditionally tumorigenic mouse cells can be spontaneous tumors arising in conventional germline transgenic mice such as those described in U.S. Pat. No. 6,639,121. Alternatively, they can be tumors arising in chimeric mice such as those described in WO 2005/020683. In either case, the genome of the tumor cells will contain: (a) an oncogene operably linked to an inducible promoter, and (b) a mutation that confers a genetic predisposition to develop cancer, e.g., a tumor suppressor knockout.

When embryonic stem cells containing the desired genetic modifications, i.e., an inducible recombinant oncogene and a second gene that confers a predisposition to develop cancer, are injected into an early stage mouse embryo, e.g., a blastocyst, the result is a chimeric mouse. See, e.g., WO 2005/020683. In addition to the above ES cell injection method, a mosaic animal also can be developed from an embryo that has been infected with viral constructs containing the desired genetic elements.

While preserving (in some percentage of its cells) the same genetic design as a conventional germline transgenic mouse, a chimeric mouse provides certain advantages. For example, to generate a conventional germline transgenic melanoma model as described in Chin et al., 1999, *Nature* 400:468-472, one would have to breed three animal lines with four respective genetic alterations, i.e., homozygous INK4a null mutation, a Tyr-rtTA transgene, and a tetO—H-ras transgene, to obtain a transgenic animal with all four genetic alterations. This extensive breeding requires a considerable amount of time. In contrast, a chimeric melanoma model requires no breeding. One needs only to establish ES cells with all four genetic alterations and inject them into a blastocyst, which develops into an intact animal upon transplantation into the uterus of a surrogate mother. The average time saved can be as much as one year. A second advantage is that in a chimeric mouse, spontaneous tumors develop in an environment that includes normal cells. This resembles the natural disease situation more closely than the cellular environment in a germline transgenic mouse, where every cell is genetically modified.

A useful ES cell line can be established by introducing more than two nucleic acid constructs into an ES cell concurrently or sequentially, where each construct may contain one or more genetic elements that will cause genetic alterations of the host genome. These genetic elements can also be inserted into one single vector, e.g., a BAC, PAC, YAC or MAC vector.

Targeted genetic alterations can introduce a desired change to a specific location in an endogenous gene. Examples of the changes include a null (knock out) mutation in a tumor suppressor gene locus or an activating mutation (knock in) to a cellular oncogene. For instance, one can replace a coding or regulatory region of a tumor suppressor gene with a selectable marker gene flanked by a pair of LoxP sites; or insert a dominant negative mutation into a tumor suppressor gene; or replace the native promoter of a cellular oncogene with a constitutive or inducible promoter; or inserting an activating mutation into a cellular oncogene (see, e.g., Johnson et al., 2001, *Nature* 410:1111-1116). Such a genetic alteration can be accomplished by homologous recombination. In a nucleic acid construct used for homologous recombination, the genetic alteration to be introduced into the host genome is flanked by sequences homologous to the targeted genomic region.

Oncogenes useful for engineering mice (germline transgenic or chimeric) to develop inducible spontaneous tumors include KRAS, HRAS, NRAS, epidermal growth factor receptor (EGFR), MDM2, TGF-β, RhoC, AKT family members, myc (e.g., c-myc), β-catenin, PDGF, C-MET, PI3K-CA, CDK4, cyclin B1, cyclin D1, estrogen receptor gene, progesterone receptor gene, Her2 (also known as neu or ErbB2), ErbB1, ErbB3, ErbB4, TGFα, ras-GAP, Shc, Nck, Src, Yes, Fyn, Wnt, Bcl2 anti-apoptotic family members, and viral proteins such as PyV MT and SV40 T antigens. Activating mutations of these oncogenes, e.g., Her2V664E, K-RasG12D, and β-cateninΔ131, also can be used.

Tumor suppressor genes whose inactivation is useful for engineering mice (germline transgenic or chimeric) to develop inducible spontaneous tumors include Rb, P53, INK4a, PTEN, LATS, Apaf1, Caspase 8, APC, DPC4, KLF6, GSTP1, ELAC2/HPC2 or NKX3.1. Other examples of tumor suppressor genes are those involved in DNA damage repair (e.g., ATM, CHK2, ATR, BRCA1, BRCA2, MSH2, MSH6, PMS2, Ku70, Ku80, DNA/PK, XRCC4 or MLH1), and cell signaling and differentiation (e.g., Neurofibromatosis Type 1, Neurofibromatosis Type 2, Adenomatous Polyposis Coli, the Wilms tumor-suppressor protein, Patched or FHIT). In addition to targeted mutation, tumor suppressor genes can be inactivated by an antisense RNA, RNA interference (RNAi), or ribozyme agent expressed from a construct stably integrated into the host genome.

Mice engineered to develop inducible spontaneous tumors for use as a source of conditionally tumorigenic cells can be developed from ES cells that contain an introduced active oncogene as well as one or more inactivated endogenous tumor suppressor gene(s). For example, the ES cells can contain genetic alterations that result in the expression of an activated form of EGFR (designated as EGFR*) in combination with reduced $p16^{INK4a}$ or $p19^{ARF}$ expression (e.g., genetic alterations that produce an EGFR*+ and INK4a/ARF$^{-/-}$ genotype); genetic alterations that result in PDGF expression in combination with reduced p53 expression (e.g., genetic alterations that produce a PDGF$^+$ and p53$^{-/-}$ genotype); genetic alterations that result in TGF-α expression in combination with reduced p53 expression (e.g., genetic alterations that produce a TGFα$^+$ and p53$^{-/-}$ genotype); and genetic alterations that result in reduced PTEN expression and reduced $p16^{INK4a}$ or $p19^{ARF}$ expression (e.g., genetic alterations that produce a PTEN$^{-/-}$ and INK4a/ARF$^{-/-}$ genotype).

An example of suitable set of genetic modifications for production of a lung cancer model is TetO-EGFR* CCSP-rtTA, p53$^{-/-}$, and PGK-puromycin (selectable antibiotic resistance marker). An example of a suitable set of genetic modifications for production of a colon cancer model is TetO-K-RAS, villin-rtTA, APC$^{-/-}$, and PGK-puromycin. An example of a suitable set of genetic modifications for production of a glioblastoma cancer model is TetO-EGFR*, Nestin-rtTA, p53$^{-/-}$, and PGK-puromycin. An example of a suitable set of genetic modifications for production of a prostate cancer model is TetO-AKT1, probasin-rtTA, Rb$^{-/-}$, and PGK-puromycin. An example of a suitable set of genetic modifications for production of a liver cancer model is TetO-β catenin, ApoE-rtTA, NF1$^{-/-}$, and PGK-puromycin.

Various vectors are useful for doing genetic manipulations and obtaining the genetically modified mouse cells necessary for practicing the present invention. Suitable vectors can be derived from plasmids, retroviruses, adenoviruses, or lentiviruses. Expression vectors typically include various genetic elements operatively linked to a polypeptide-encoding heterologous nucleic acid insert. Examples of such genetic elements are those that affect transcription and RNA processing, e.g., operators, silencers, promoters and enhancer elements, transcription termination signals, RNA splicing signals and polyadenylation signals. Other signals affect translation, e.g., ribosomal consensus sequences. The use of such expression control elements, including those that confer constitutive or inducible expression, and developmental or tissue-specific expression are known in the art.

The vectors can be introduced into mouse cells, including ES cells and tumor cells, by various methods, including cell fusion (e.g., spheroplast fusion), liposome fusion (transposomes), conventional nucleic acid transfection methods such as calcium phosphate precipitation, electroporation, microinjection, or infection by viral vectors. Various methods can be used to screen for cells that have stably incorporated the desired genetic alterations. Such methods include detection of drug resistance where a drug selection marker gene (e.g., a neomycin-resistant gene, a puromycin-resistant gene, or a hygromycin-resistant gene) is co-introduced; detection of fluorescence or bioluminescence emission where a fluorescence or bioluminescence marker gene (e.g., a gene encoding a green, yellow, blue or red fluorescent protein, and Luciferase genes) is co-introduced; polymerase chain reaction (PCR); and Southern blot analysis.

Recombinant genes, e.g., a recombinant oncogene or a gene of interest, can be placed under the control of an inducible promoter such as the tetracycline-regulated promoter system as described in e.g., WO 01/09308. Complete tetracycline-regulated mammalian expression systems are available commercially, e.g., T-Rex™, Invitrogen, Carlsbad, Calif. When using such a system, the inducing agent (e.g., tetracycline or doxycycline) can be administered conveniently in food or drinking water. Other useful inducible promoters include the metallothionine promoter, the IPTG/lacI promoter system, the ecdysone promoter system, and the Gal4/UAS system, which is available commercially, e.g., GeneSwitch™, Valentis, Inc., Burlingame, Calif. The "lox stop lox" system can be used to delete inhibitory sequences, thereby irreversibly inducing expression of a particular gene to commence in a particular tissue at a particular point in development of the mouse. For a discussion of inducible promoters in transgenic mouse cells and transgenic mice, see Lewandoski, 2001, "Conditional Control of Gene Expression in the Mouse," *Nature Rev.* 2:743-755.

Recombinant genes introduced into mouse cells can be placed under the control of a tissue-specific promoter, such as a tyrosinase promoter or a TRP2 promoter in the case of melanoma cells and melanocytes; an MMTV or WAP promoter in the case of breast cells and/or cancers; a Villin or FABP promoter in the case of intestinal cells and/or cancers; a PDX promoter in the case of pancreatic cells; a RIP promoter in the case of pancreatic beta cells; a Keratin promoter in the case of keratinocytes; a Probasin promoter in the case of prostatic epithelium; a Nestin or GFAP promoter in the case of central nervous system (CNS) cells and/or cancers; a Tyrosine Hydroxylase, S100 promoter or neurofilament promoter in the case of neurons; the pancreas-specific promoter described in Edlund et al., 1985, *Science* 230:912-916; a Clara cell secretory protein promoter in the case of lung cancer; and an Alpha myosin promoter in the case of cardiac cells.

Developmentally regulated promoters also can be used in practicing the invention. They include the murine hox promoters (Kessel et al., 1990, *Science* 249:374-379) and the α-fetoprotein promoter (Campes et al., 1989, *Genes Dev.* 3:537-546).

Any ES cell lines that provide adequate chimerism can be used. Useful cell lines include E14.1, WW6, CCE, J1, and AB1. See also Alex Joyner, Ed., *Gene Targeting, A Practical Approach*, Chapter 4 (Virginia Papaioannou), Oxford Press, $2^{nd}$ Ed., (2000). In general, when chimeric mice are used, the extent of chimerism is not critical. Chimerism of 10% to 90% is preferred.

As used herein, "chimeric" means chimeric in terms of ontogeny. Accordingly, a chimeric mouse is a mouse that has grown, i.e., developed, directly from a multicellular embryo into which at least one genetically modified ES cell has been injected or aggregated. A chimeric mouse is to be distinguished from a morphologically developed mouse that has received a xenograft, e.g., an organ graft, a tissue graft, or a tumor graft from another animal.

A chimeric mouse can be generated by introducing ES cells containing into a host embryo. This can be done, for example, by blastocyst injection or aggregation with earlier stage pre-implantation embryos (e.g., eight-cell embryo). The embryo is subsequently transferred into a surrogate mother for gestation. Chimerism in the born animal can be determined by phenotype (such as fur color, if the host embryo and the ES cells are derived from animal strains of different fur colors), PCR, Southern blot analysis, or biochemical or molecular analysis of polymorphic genes (such as glucose phosphate isomerase). To facilitate identification of chimeric mice having a desired genetic alteration, one can co-introduce a detectable reporter gene and the desired genetic alteration into the ES cells. Exemplary reporter genes include those that encode a fluorescent protein such as a green fluorescent protein, a yellow fluorescent protein, a blue fluorescent protein, or a luminescent protein such as luciferase or β-galactosidase.

To increase the contribution of introduced ES cells to a specific tissue, one can use a host embryo that is deficient in generating that issue. This can be accomplished by any suitable method, including inducible expression of a toxin gene, e.g., diphtheria toxin, in a specific cell type, or tissue-specific deletion of genes needed for generating this cell type. In such a complementation system, all or most of the cells of the desired cell type or tissue will be derived from the introduced ES cells.

The chimeric mice provide flexibility in developing models of different diseases. For example, ES cell lines can be established for different cancer models by knocking out both alleles of a tumor suppressor gene (e.g., p53) and introducing a reporter gene (e.g., luciferase), a tissue-specific reverse tetracycline transactivator gene (i.e., MMTV-rtTA) and an oncogene of choice (e.g., Akt, Her2V664E, Her2, Bcl2, K-Ras and Cyclin D1) under the control of a promoter regulated by reverse tetracycline transactivator (rtTA).

Introduction of the recombinant gene of interest into the conditionally tumorigenic mouse cell can be by any suitable method. Various methods are known in the art, e.g., retroviral vectors, lentiviral vectors, lipofection and electroporation. A preferred method is transduction using a retroviral vector. Preferably, the tumor cells are removed from a donor mouse, subjected to a transduction procedure (or other method of introducing the recombinant gene of interest), and placed into a recipient mouse within 48 hours. It has been found that putting the cells back into an animal within 48 hours preserves the inducibility of the oncogene. Loss of inducibility sometimes is observed, when the cells are maintained in vitro for longer periods.

Figure 2:
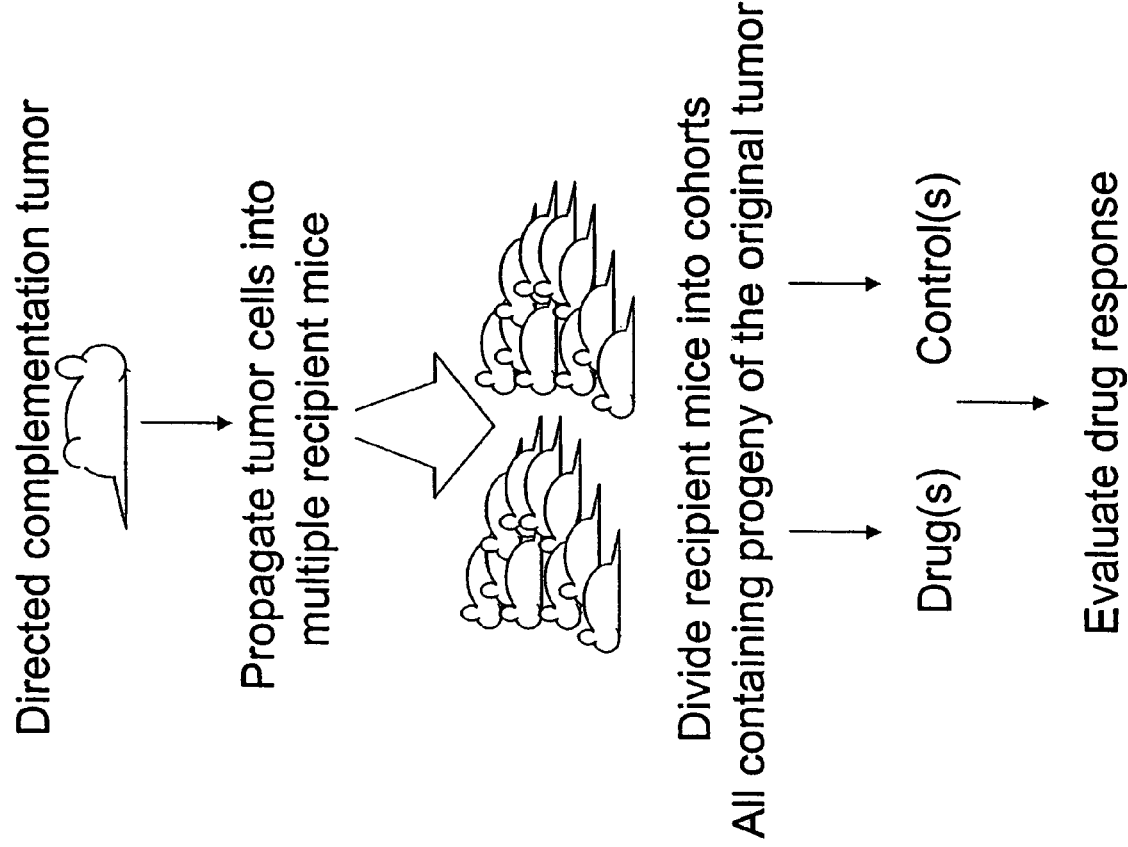
FIG. 2 is a schematic drawing illustrating the in vivo propagation and "amplification" of tumor material for use in drug response studies.
Figure 3:
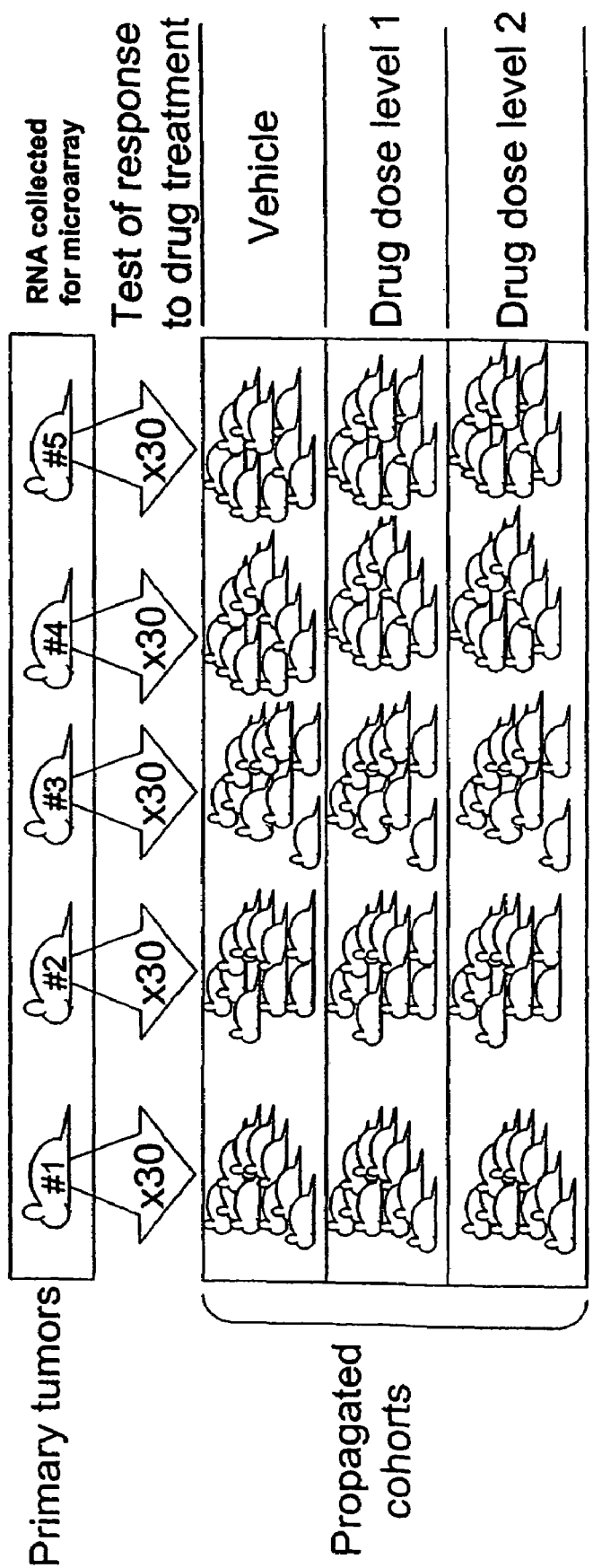
FIG. 3 is a schematic drawing illustrating one basic experimental design for a drug response test according to the present invention.

Once the transduced cells give rise to a directed complementation tumor in the initial recipient mouse, directed complementation tumor material (tumor cells) can be propagated into multiple recipient mice, which can be divided into cohorts, all containing progeny of the original directed complementation tumor (FIG. 2). Optionally, samples of primary tumor material can be taken at this point for RNA preparation and microarray analysis. Utilizing the present invention, drug response tests can be designed in such a way, and with sufficient numbers of tumor-bearing mice, to allow statistical analysis of results (FIG. 3). This allows observation of inter-tumoral variation and intra-tumoral uniformity.

As used herein, "test compound" means macromolecules, e.g., polypeptides, nucleic acids, polysaccharides and lipids, as well as small molecules. Test compounds can be administered to host mice comprising reconstituted human breast tumor models of this invention through oral, rectal, vaginal, topical nasal, ophthalmic or parenteral administration. Parenteral administration includes subcutaneous, intravenous, intramuscular, and intrastemal injection, and infusion techniques. An exemplary route of administration for mouse experimentation is injection into the tail vein.

Preferably, test compounds are formulated in a manner that takes into account factors such as the dosage, compound solubility and route of administration. Solid formulations for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, e.g., microcrystalline cellulose, corn starch, sodium starch glycolate, and alginic acid. Tablet binders include acacia, methylcellulose, sodium carboxymethylcellulose, polyvinylpyrrolidone (Povidone™), hydroxypropyl methylcellulose, sucrose, starch, and ethylcellulose. Examples of lubricants include magnesium stearates, stearic acid, silicone fluid, talc, waxes, oils, and colloidal silica.

Liquid formulations for oral administration prepared in water or other aqueous vehicles can contain suspending agents such as methylcellulose, alginates, tragacanth, pectin, kelgin, carrageenan, acacia, polyvinylpyrrolidone, and polyvinyl alcohol. The liquid formulations also can include solutions, emulsions, syrups and elixirs containing, together with the active compound(s), wetting agents, sweeteners, and flavoring agents. Injectable formulations can contain carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). Physiologically acceptable excipients include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution.

A suitable insoluble form of the compound can be prepared and administered as a suspension in an aqueous base or a pharmaceutically acceptable oil base, such as an ester of a long chain fatty acid (e.g., ethyl oleate). A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens. Pharmaceutical formulation is a well-established art, and is further described in Gennaro (ed.), Remington: *The Science and Practice of Pharmacy,* 20th ed., Lippincott, Williams & Wilkins (2000) (ISBN: 0683306472); Ansel et al., *Pharmaceutical Dosage Forms and Drug Delivery Systems,* 7th ed., Lippincott Williams & Wilkins Publishers (1999) (ISBN: 0683305727); and Kibbe (ed.), *Handbook of Pharmaceutical Excipients* American Pharmaceutical Association, 3rd ed. (2000) (ISBN: 091733096X).

Numerous parameters can be employed to determine whether a test compound displays "an anti-tumor effect." Examples of such parameters include amount of apoptosis in the tumor tissue, level of angiogenesis in the tumor tissue, number of hyperplastic growths such as ductal hyperplasias, effects on differentiation or morphogenesis of the tumor tissue, or simply the size, e.g., diameter or volume of the tumor. The choice of parameter(s) to be measured, and their interpretation, will depend on the objectives of the particular experiment. Such choice and interpretation is within ordinary skill in the art.

There is considerable latitude in experimental design. For example, in one type of experimental design, test animals and control animals may be separate and substantially identical. In another type of experimental design, test compound and vehicle may be administered locally to separate tumors, e.g., left side and right side, on the same animal. Of course, a panel of animals can receive a range of dosages in dose-response studies.

EXAMPLES

The invention is further illustrated by the following examples. The examples are provided for illustrative purposes only, and are not to be construed as limiting the scope or content of the invention in any way.

Example 1

Spontaneous Inducible Tumors

Chimeric mice were engineered to develop Her2-dependent, inducible spontaneous breast tumors for use as a source of conditionally tumorigenic cells. The mice were produced as follows.

Ink4a homozygous null ES cells were co-transfected with the following four constructs, as separate fragments: MMTV-rtTA, TetO-Her2$^{V664Eneu}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

The mouse mammary tumor virus long terminal repeat (MMTV) was used to drive breast-specific expression of the reverse tetracycline transactivator (rtTA). The rtTA provided for breast-specific expression of the HER2 activated oncogene when doxycycline was provided to the mice, e.g., in their drinking water.

Inducibility of the HER2 oncogene and luciferase was confirmed by RT-PCR and luciferase assay (respectively), using cultured cells derived from the mouse. Mammary glands were removed from chimeric mice and digested with collagenase. Half of the organoids collected were cultured in the presence of doxycycline, and the other half was cultured without doxycycline. After five days in culture, the cells were trypsinized, and one tenth of the cells were used for luciferase assay, and the rest were used for RNA extraction.

The histology analysis of tumors harvested from HER2 breast cancer model mice showed invasive adenocarcinomas. Two major patterns were distinguished. They were a solid sheet growth pattern, and a nested growth pattern with necrotic centers.

Immunohistochemistry analysis of mammary tumors from HER2 breast cancer model mice revealed two cell types within the tumors. The first cell type was epithelial origin (cytokeratin positive), and showed HER2 expression and strong proliferation. The second cell type was mesenchymal origin with fibroblast-like appearance. These cells were collagen positive. These cells did not show strong proliferation, and they displayed stromal function. Apoptosis was seen in the necrotic centers of the epithelial part of the tumors.

Tumor regression studies were performed using the HER2 breast cancer model mice. Two mice, each carrying more than two doxycycline-induced tumors, were selected. The tumor size of two tumors each was measured using calipers before and after doxycycline was withdrawn from the drinking water. Doxycycline was withdrawn at day six. Tumor size was measured daily. The tumor size measurements were used to calculate the tumor volume. Results were plotted and the regression of the tumors was determined. All tumors regressed, displaying doxycycline-dependence. Immunohistochemistry analysis of tumor regression confirmed doxycycline-dependent HER2 expression. Thus, growth and maintenance of the tumors were shown to depend on HER2 expression.

Example 2

Tumor Propagation

Following induction of the tetracycline-responsive promoter by doxycycline, the mice developed mammary tumors with a latency of about 2-4 months. Approximately five primary breast tumors were size-selected (>0.4 g) from one animal (two from thoracic and three from inguinal glands) so as to provide enough tumor cells for propagation.

About 0.2 g of surgically resected primary tumours were minced and digested with 1.5 ml of digestion mix (4 mg/ml collagenase; Calbiochem cat. No. 234153) in RPMI media (Gibco cat. No. 11875-093) in a 10 ml polypropylene tube for about 2 hours at 37° C. with constant shaking at 400 rpm. The digested tissues were triturated by passing them through 18 gauge needle or using cell strainers (40 µm (BD Falcon, cat. No. 352340) and 100 µm (BD Falcon cat. No. 352360) filters). The resultant cell mix was let stand at room temperature for about five minutes, followed by aspiration of only the top portion without disturbing the undigested coarse material at the bottom. The cells were centrifuged at 1000 rpm for 5 minutes, washed twice with RPMI and counted using hemocytometer and either resuspended in HBSS (Gibco cat. No. 24020-117) for injections, or resuspended in freezing media (90% FBS [Gibco cat. No. 10438-026]+10% DMSO), followed by serial temperature shift-down to liquid nitrogen storage for future use.

From each primary tumor, about 0.1 million cells/site were injected sub-cutaneously into 30 sites on immunocompromised mice, which were then fed with doxycycline water. Each mouse received two injections, one on each side of its back (subcutaneous). Thus, one primary tumor was expanded into 30 propagated tumors onto 15 mice, each of the mice developing two tumors on its back. Out of these thirty tumors, 10 tumor-bearing mice were treated with vehicle (5 parts Tween-80, 5 parts absolute ethyl alcohol, 90 parts 5% dextrose), another 10 tumor bearing-mice were treated with 15 mg/kg docetaxel (Biochemika, cat. No. 01885), and the remaining 10 tumor-bearing mice were treated with 30 mg/kg docetaxel (which was already determined to be near MTD for this drug). In total, five primary tumors were expanded to 150 tumors in 75 animals.

Example 3

Drug Response Assay

When the tumors reached approximately 5 mm$^3$ in size, the treatments were begun. The animals were given three doses with 5-day intervals. The experiment was terminated one week after the final dosing. Among propagated tumors derived from any given primary tumor, uniformity in terms of latency, growth rate and drug response was expected (intra-tumoral uniformity). In contrast, among propagated tumors derived from different primary tumors variation in terms of growth rate, latency and drug response was expected (inter-tumoral variation).

As expected, intra-tumoral uniformity and inter-tumoral variation in the latency and drug response from the propagated tumors was observed. It was scored as a positive response if a tumor showed a statistically significant difference in size between vehicle and drug treatment at the end of one week after last dosing. Propagated tumors that came from only one of the five primary tumors showed significant reduction in tumor growth to the drug treatment while the remaining four groups did not show any effect.

Example 4

Preparation of Conditionally Tumorigenic Cells for Transfection

A mouse breast HER2 tumor was surgically removed (avoiding excessive bleeding) and placed immediately on PBS in a Petri dish. The size and weight of the tumor were measured using a caliper and a balance. Approximately 0.2 g of tumor tissue was transferred to a Petri dish and chopped into fine pieces. To the minced tumor pieces, 1.5 ml digestion mix (4 mg/ml collagenase in RPMI 1640 media) was added and transferred on to a 10 ml polypropylene tube, followed by incubation at 37° C. with constant shaking at 400 rpm for 2 hours. Digested tumor material was passed through an 18 G needle 5-10 times. Coarse particulate matter was allowed to settle for about 5 minutes, and then liquid was aspirated without disturbing the undigested coarse material at the bottom. A cell suspension was spun down at 1000 rpm for 5 minutes, washed twice using RPMI, and counted using hemocytometer.

The cells were plated onto 10 cm or 15 cm Petri dish, and fed with fresh media the next day, followed by feeding as necessary. Once the cells started attaching to the plate and became confluent upon multiplying, they were dispersed onto additional plates using 0.05% Trypsin/EDTA. The cells generally adapted to culture upon two such passages. Upon completion of two passages, the cells were harvested and cryopreserved at −80° C. in freezing media (90% DMSO/10% FBS) for future use. The cultures generated using this approach were tested for the ability to produce tumors in vivo upon oncogene induction, i.e., they were tested for conditional tumorigenic status.

To test the conditional inducibility of oncogene expression in these cells in vitro, the cells were cultured in the presence of inducer (doxycycline) and monitored for the modulated oncogene induction in the presence and absence of the inducer. To assess conditional tumorigenic status in vivo, the cells were cultured in the presence of doxycycline and injected sub-cutaneously into six immuno-compromised mice ($1 \times 10^6$ cells per injection site, two sites per mouse). Doxycycline was administered to three of the six mice through food or water. The remaining three mice were maintained on food and water without doxycycline. The animals were monitored for tumor growth. Only the animals that received doxycycline developed tumors at the site of injection. After the tumors reached a volume of 500 mm³, the doxycycline was withdrawn from the food/water. This caused regression of the tumor growth, indicating that the cells of these tumors required the expression of the oncogene to remain tumorigenic. These conditionally tumorigenic cells were then used for directed complementation, using a recombinant oncogene, as described in Example 5 (below).

Example 5

Directed Complementation in Breast Tumor Cells

Vector constructs Retroviral vectors were used for transduction of mouse breast tumor cells prepared as described in Example 4 (above). The retrovirus backbone used in constructing all of the following retroviral vectors was either pQCXIX, which was obtained commercially (BD Biosciences Clontech; Palo Alto, Calif.; cat. # 9135-1) or pBMN-GFP, which is commercially available from Orbigene Inc. (San Diego, Calif.; cat# PVL-10014).

The vector pQCDIG was constructed as follows. A 1452 bp IRES-hrGFP DNA fragment was obtained by digesting the pIRES-hrGFP II vector (Stratagene, San Diego, Calif.; cat # 240032) with BamHI and XhoI. The IRES-hrGFP fragment was then cloned behind the CMV promoter in the vector pQCXIX. The resulting vector was then digested with NotI and treated with Klenow DNA polymerase and calf alkaline phosphatase (New England Biolabs, Beverly, Mass.) to generate clonable blunt ends. A 1.7 kb DNA fragment containing Gateway® destination reading frame cassette (Invitrogen, Carlsbad, Calif.; cat # 11828-029) was then cloned into the NotI digested vector to generate retroviral construct pQCDIG.

The vector pBGD-1 was constructed as follows. Vector pBMN-GFP was digested with EcoRI and treated with Klenow polymerase to generate blunt ends. The vector was then ligated with Gateway® destination reading frame cassette Rfc.1 (Invitrogen, Carlsbad, Calif.; cat# 11828-029) to generate retroviral construct pBGD-1.

The vector pQ-LacZ and pB-LacZ were constructed as follows. A 3.1 kb LacZ cDNA fragment (Marker Gene Technology, Inc., Eugene, Oreg.; cat # M1016) was cloned into vector pENTR11 (Invitrogen; cat # 11819-018) to generated vector pENTR-LacZ. Gateway® LR recombination reaction was performed between vector pENTR-LacZ and vector pQCDIG or pBGD-1. The resulting vector pQ-LacZ or pB-LacZ was confirmed by restriction enzyme digestion and nucleic acid sequencing.

The vector pQ-HER2 and pB-HER2 were constructed as follows. A 3992 HER2 cDNA fragment was cloned into vector pENTR11 (Invitrogen, cat # 11819-018) to generated vector pENTR-HER2. The HER2 cDNA used in making this construct was ErrB2$^{V659E}$. The accession number for wild type HER2 cDNA is M11730. Site directed mutagenesis was employed to change amino acid residue 659 from V to E. Gateway® LR recombination reaction was performed between vector pENTR-HER2 and vector pQCDIG or pBGD-1. The resulting vector pQ-HER2 or pB-HER2 was confirmed by restriction enzyme digestion and nucleic acid sequencing.

The vector pB-ERBB3 was constructed as follows. A 4.2 kb human ERBB3 cDNA fragment (ATCC, Manassas, Va.; cat# 8117300) was cloned into vector pENTR11 (Invitrogen; cat#1819-018) to generated vector pENTR-ERBB3. Gateway® LR recombination reaction was performed between vector pENTR-ERBB3 and vector pBGD-1. The resulting vector pB-ERBB3 was confirmed by restriction enzyme digestion and nucleic acid sequencing.

The vector pB-PLK3 was constructed as follows. A 2.1 kb human PLK3 cDNA fragment (OriGene, Rockville, Md., cat# TC117577) was cloned into vector pENTR11 (Invitrogen; cat#11819-018) to generated vector pENTR-PLK3. Gateway® LR recombination reaction was performed between vector pENTR-PLK3 and vector pBGD-1. The resulting vector pB-PLK3 was confirmed by restriction enzyme digestion and nucleic acid sequencing.

The vector pB-Kirrel was constructed as follows. A 1.8 kb mouse Kirrell cDNA fragment (ATCC, Manassas, Va.; cat# MGC-38329) was cloned into vector pENTR11 (Invitrogen; cat# 11819-018) to generated vector pENTR-Kirrel. Gateway® LR recombination reaction was performed between vector pENTR-Kirrel and vector pBGD-1. The resulting vector pB-Kirrel was confirmed by restriction enzyme digestion and nucleic acid sequencing.

The vector pB-MET was constructed as follows. A 4.2 Kb human MET cDNA fragment (OriGene, Rockville, Md., cat# TC120029) was cloned into vector pENTR11 (Invitrogen; cat#11819-018) to generate vector pENTR-MET. Site-directed mutagenesis was employed to change base 3717 from G to A to correct a point mutation. Gateway® LR recombination reaction was performed between vector pENTR-MET and vector pBGD-1. The resulting vector pB-MET was confirmed by restriction enzyme digestion and nucleic acid sequencing.

The vector pB-HGF was constructed as follows. A 2.2 Kb human HGF cDNA fragment (Invitrogen, clone ID# IOH29794) was cloned into vector pENTR11 (Invitrogen, cat # 11819-018) to generate vector pENTR-HGF. Gateway® LR recombination reaction was performed between vector pENTR-HGF and vector pBGD-1. The resulting vector pB-HGF was confirmed by restriction enzyme digestion and nucleic acid sequencing.

The vector pB-ESM1 was constructed as follows. A 550 bp human ESM1 cDNA fragment was cloned into vector pENTR11 (Invitrogen, cat # 11819-018) to generated vector pENTR-ESM1. Gateways® LR recombination reaction was performed between vector pENTR-HGF and vector pBGD-1. The resulting vector pB-ESM1 was confirmed by restriction enzyme digestion and nucleic acid sequencing.

The vector pB-PTK7 was constructed as follows. A 3.2 Kb human PTK7 cDNA fragment was cloned into a modified (NcoI deletion) vector pENTR11 (Invitrogen, cat # 11819-018) to generate vector pENTR-PTK7. Gateway® LR recombination reaction was performed between vector pENTR-HGF and vector pBGD-1. The resulting vector pB-PTK7 was confirmed by restriction enzyme digestion and nucleic acid sequencing.

Ecotropic Retrovirus Ecotropic retrovirus packaging cell line EcoPack2-293 and Phoenix™ were obtained commercially (BD Biosciences Clontech; Palo Alto, Calif.; cat# 631507) and Orbigene Inc. (San Diego, Calif.; cat# PVL-10014). EcoPack2-293 cells or Phoenix™ cells were cultured in DMEM medium (containing 10% FBS, 50 U/ml penicillin, 50 µg/ml streptomycin) until 70% confluent. 20 µg DNA of retroviral vector was transfected into EcoPack2-293 or Phoenix™ cells using Fugene6 transfection reagent (Roche Applied Science, Indianapolis, Ind.; cat # 11814443001). Transfection efficiency was monitored by green fluorescent protein (GFP) visualization 24 hours after transfection. Retrovirus was harvested 48 hours after transfection by filtering medium supernatant through 0.45 micron filter and stored in −80° C.

Retroviral infection of tumor cells Mouse breast HER2 tumor cells were cultured in RPMI 1640 medium (containing 10% FBS, 50 U/ml penicillin, 50 µg/ml streptomycin and 2 µg/ml doxycycline). At approximately 18-24 hours after plating, or when the plated cells were 70-80% confluent, the breast tumor cells were infected with thawed retroviral supernatant in the presence of polybrene (8 µg/ml) for approximately 8 hours. Upon the removal of the medium, fresh medium was added overnight and this procedure was repeated the next day. When cells were infected with two different viruses, one virus was added the first day and the other the second day.

Functional complementation Approximately 24 hours after the addition of the second batch of virus, infected breast tumor cells were trypsinized, rinsed and resuspended in Hank's Balanced Salt Solution. About $1 \times 10^6$ infected tumor cells were injected into the flank of SCID mice maintained without doxycycline. The animals were observed for tumor development. Control animals maintained without doxycycline were similarly injected with $1 \times 10^6$ uninfected tumor cells or $1 \times 10^6$ breast tumor cells infected with pQ-LacZ retrovirus.

Tumors complemented with pQ-HER2 or pB-HER2 retrovirus developed after approximately 14 days in 6 out of 6 injection sites. No tumor was observed on mice injected with either breast tumor cells or breast tumor cells infected with pQ-LacZ or pB-LacZ retrovirus during the experiment period. Tumors were harvested and tumor tissues were immediately snap-frozen in liquid nitrogen. RNA was isolated from tumor tissue and real-time PCR was performed to confirm the expression of target gene by using target gene specific primers. Human HER2 expression level in complemented tumors was about 10-15 fold higher than normal human reference, similar to doxycycline-induced tumors. The expression of retroviral constructs in tumor cells was also confirmed by GFP protein immunohistochemistry on formalin fixed tumor samples.

Tumors complemented with pB-ERBB3 retrovirus were observed after approximately 26 days in 15 out of 18 injection sites. Human ERBB3 expression level in complemented tumors was examined by real time PCR, which was about 5-20 fold higher than normal human reference. The expression of retroviral constructs in tumor cells was also confirmed by GFP protein immunohistochemistry on formalin fixed tumor samples.

Tumors complemented with pB-PLK3 retrovirus were observed after approximately 28 days in 3 out of 6 injection sites. Human PLK3 expression level in complemented tumors was examined by real time PCR, which was about 2-5 fold higher than normal human reference. The expression of retroviral constructs in tumor cells was also confirmed by GFP protein immunohistochemistry on formalin fixed tumor samples.

Tumors complemented with pB-Kirrel retrovirus were observed after approximately 31 days in 3 out of 6 injection sites. Mouse Kirrell expression level in complemented tumors was examined by real time PCR, which was about 10-25 fold higher than normal mouse reference. The expression of retroviral constructs in tumor cells was also confirmed by GFP protein immunohistochemistry on formalin fixed tumor samples.

Figure 4:
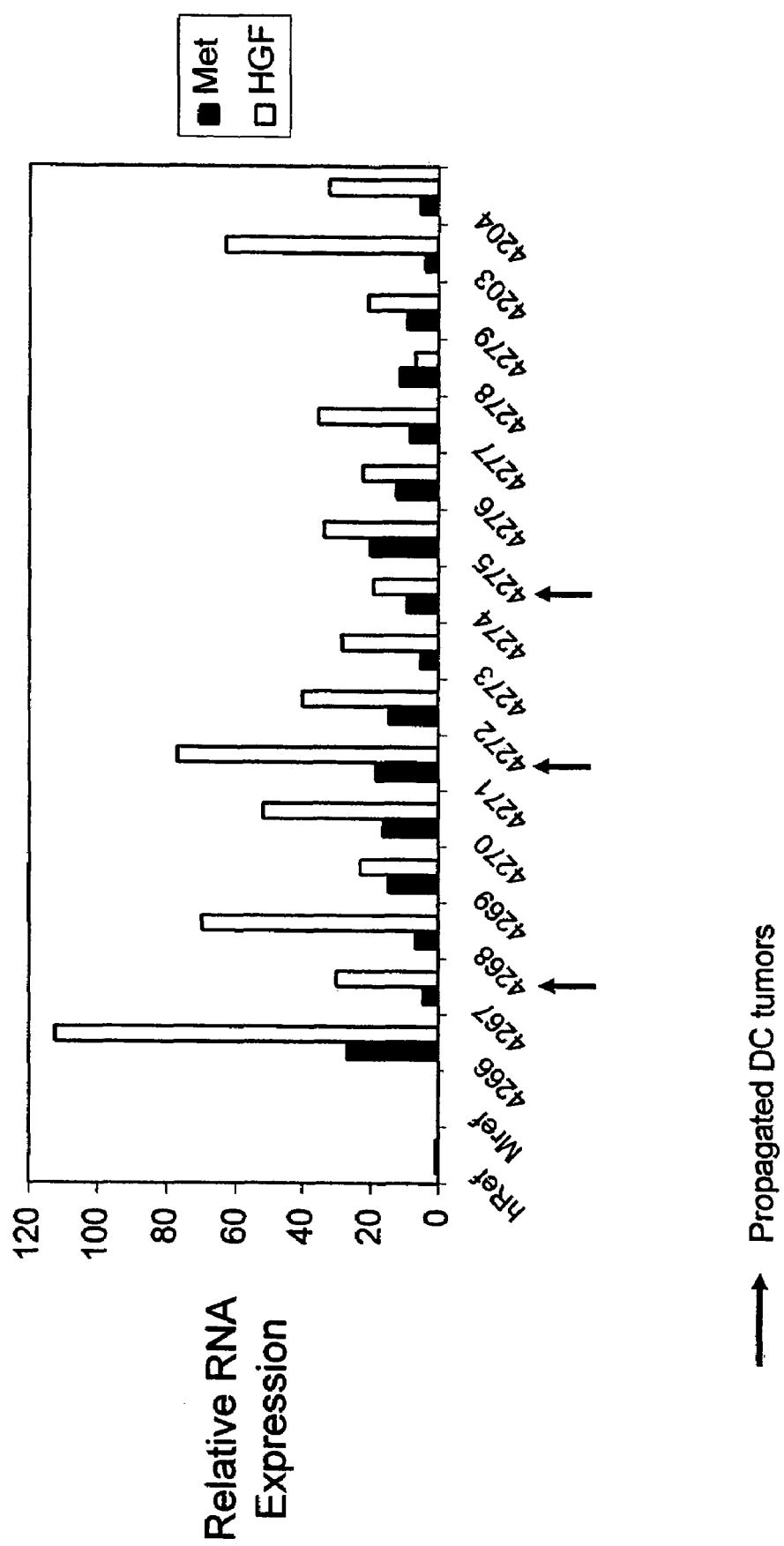
FIG. 4 is a histogram illustrating the human MET (hMET) and human HGF (hHGF) mRNA levels in MET/HGF-Direct Complemented (DC) tumors. The real time PCR (RT-PCR) levels for human and mouse control reference RNA (hRef and Mref) and 14 independently generated MET/HGF DC tumors are illustrated. The arrows indicate hMEG/hHGF DC tumors selected for subsequent propagation studies.

Tumors complemented with both pB-MET and pB-HGF retroviruses were observed after approximately 30 days in 14 out of 20 injection sites. Human MET and human HGF expression levels in the resulting complemented tumors (MET/HGF) were examined by real time PCR, which was about 5-25 fold higher and about 20-80 fold higher than normal human reference, respectively (FIG. 4). This example demonstrates that complemented tumors can be generated by the simultaneous introduction of multiple genes into the recipient cells.

Tumors complemented with pB-ESM1 retrovirus were observed after approximately 41 days in 3 out of 6 injection sites. Human ESM1 expression levels in complemented tumors was examined by real time PCR, which was about 180-300 fold higher than normal human reference.

A tumor complemented with pB-PTK7 retrovirus was observed after approximately 40 days in 1 out of 6 injection sites. Human PTK7 expression level in the complemented tumor was examined by real time PCR, which was about 6 fold higher than normal human reference.

Example 6

In Vivo Propagation of Directed Complementation Tumors

Directed Complementation (DC) tumors were propagated in vivo. About 0.2 g of surgically resected direct complemented tumor was minced and resuspended in freezing media (90% FBS [Gibco Cat. No. 10438-026]+10% DMSO), followed by serial temperature shift-down to liquid nitrogen storage for future use.

Minced DC tumor was thawed at 37° C. and cells were dissociated by passing through cell strainers (100 µm filters, BD Falcon Cat. No. 352360). The cells were collected and centrifuged at 1000 rpm for 5 minutes, washed twice with PBS and counted using hemocytometer and resuspended in one part PBS (Gibco Cat. No. 24020-117) to one part Matrigel (BD Cat. No 3542334) for injections. About 0.1 million cells were injected sub-cutaneously into 10 immunocompromised mice, at a single site per mouse.

Figure 5:
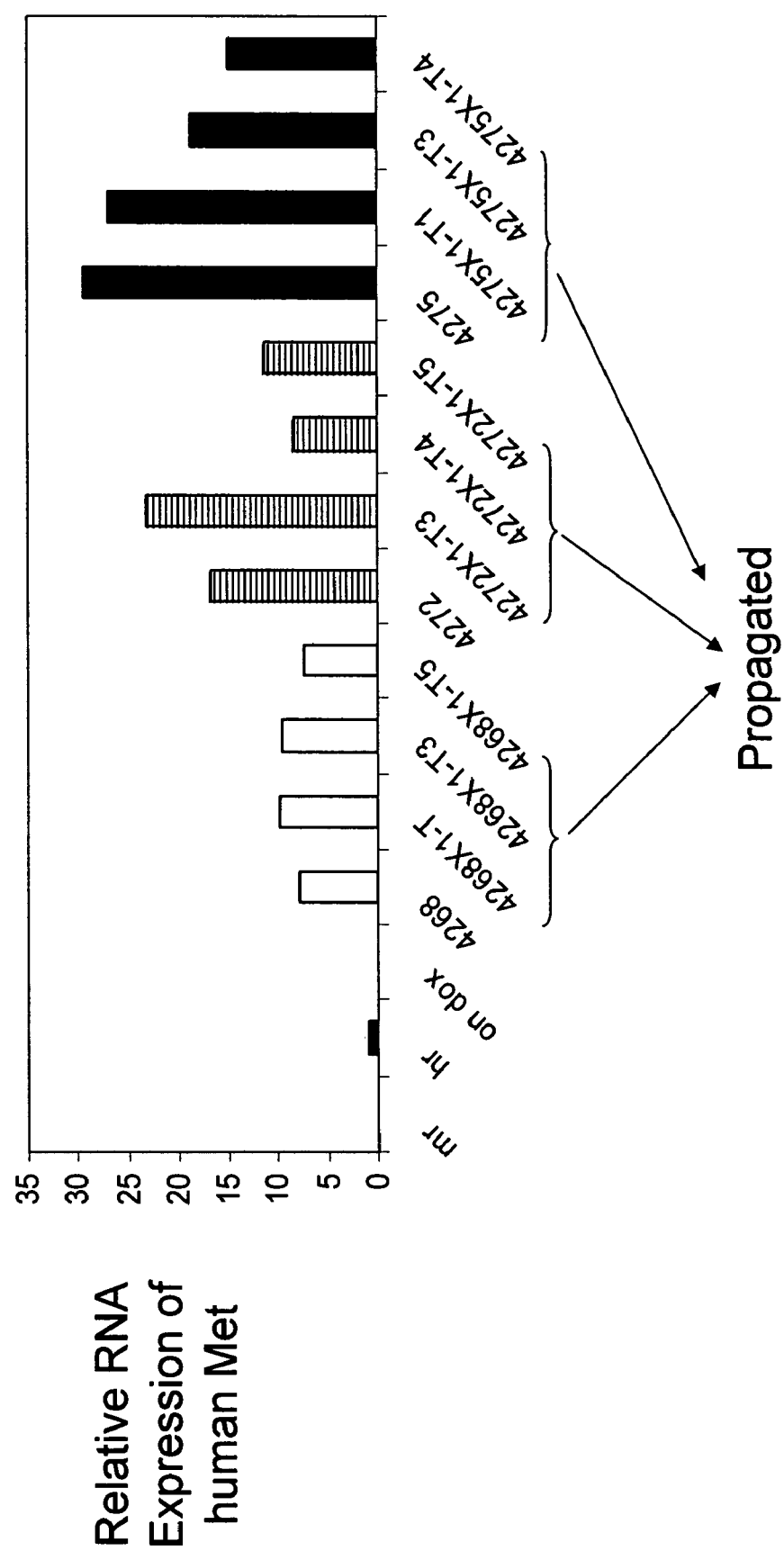
FIG. 5 is a histogram illustrating the hMET mRNA levels in MET/HGF-DC tumors and subsequent propagation. The RT-PCR analysis was performed on three independently generated MET/HGF direct complemented tumors and their propagated samples. Human universal reference (hr) RNA was used as a positive control and mouse RNA universal referance (mr) and ON DOXY (on dox) tumor RNA were used as negative controls.
Figure 6:
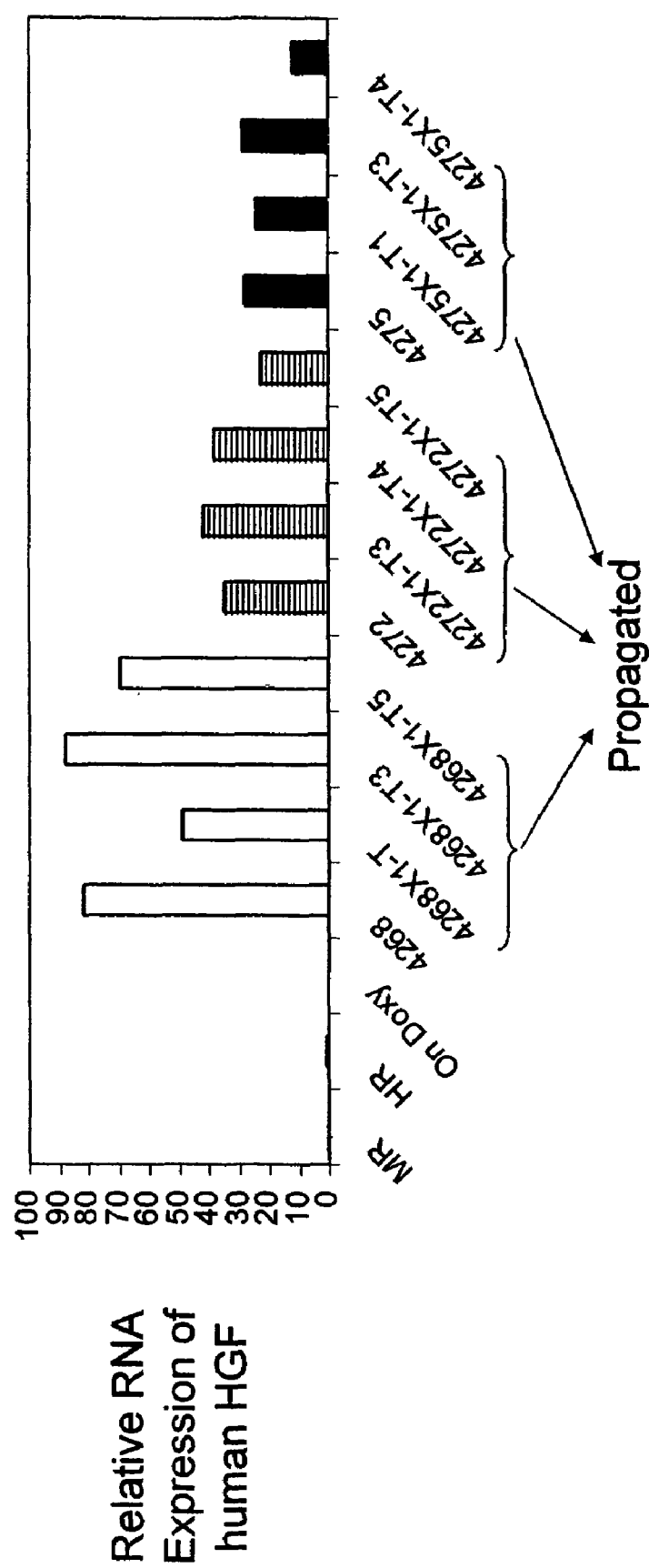
FIG. 6 is a histogram illustrating the hHGF mRNA levels in MET/HGF-DC tumors and subsequent propagation. The RT-PCR analysis was performed on three independently generated MET/HGF direct complemented tumors and their propagated samples. Human universal reference (hr) RNA was used as a positive control and mouse RNA universal referance (mr) and ON DOXY (on dox) tumor RNA were used as negative controls.

Propagated MET/HGF complemented tumors were observed after approximately 24 days in 10 out of 10 injection sites. Human MET and human HGF expression levels in the propagated direct complemented tumors (MET/HGF) were examined by real time PCR, which was about 5 to 25 fold higher and about 15-90 fold higher than normal human reference, respectively (FIGS. 5 and 6). Human MET protein levels were also confirmed by Western Blot analysis (not shown). Human HGF levels were confirmed by capture Elisa (FIG. 7). This example shows how DC tumors can be propagated in vivo, and that overexpression of both transgenes were maintained upon propagation.

Example 7

Drug Response Assay with Directed Complementation Tumors

Figure 8:
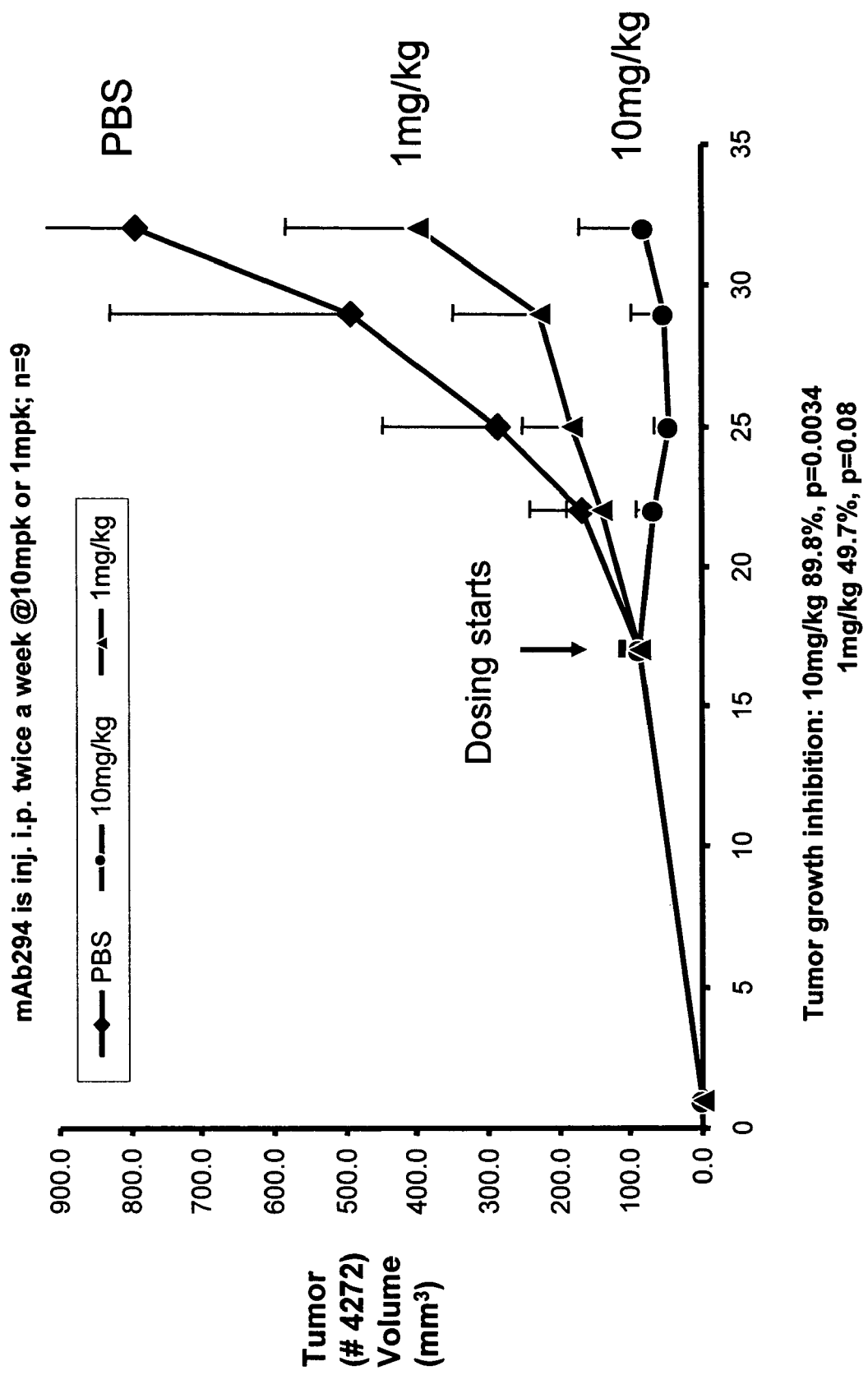
FIG. 8 is a graph summarizing data on the effect of the anti-HGF antibody (mAb294) on the growth of the breast Her2 derived MET/HGF complemented tumor 4272. Anti-HGF antibody (mAb294) was injected at either 10 mg/kg or 1 mg/kg intraperitoneally into breast Her2 derived MET/HGF complemented tumor 4272 twice a week. The effect of the antibody treatment on tumor volume was measured over 30 days. PBS was used as a control.
Figure 9:
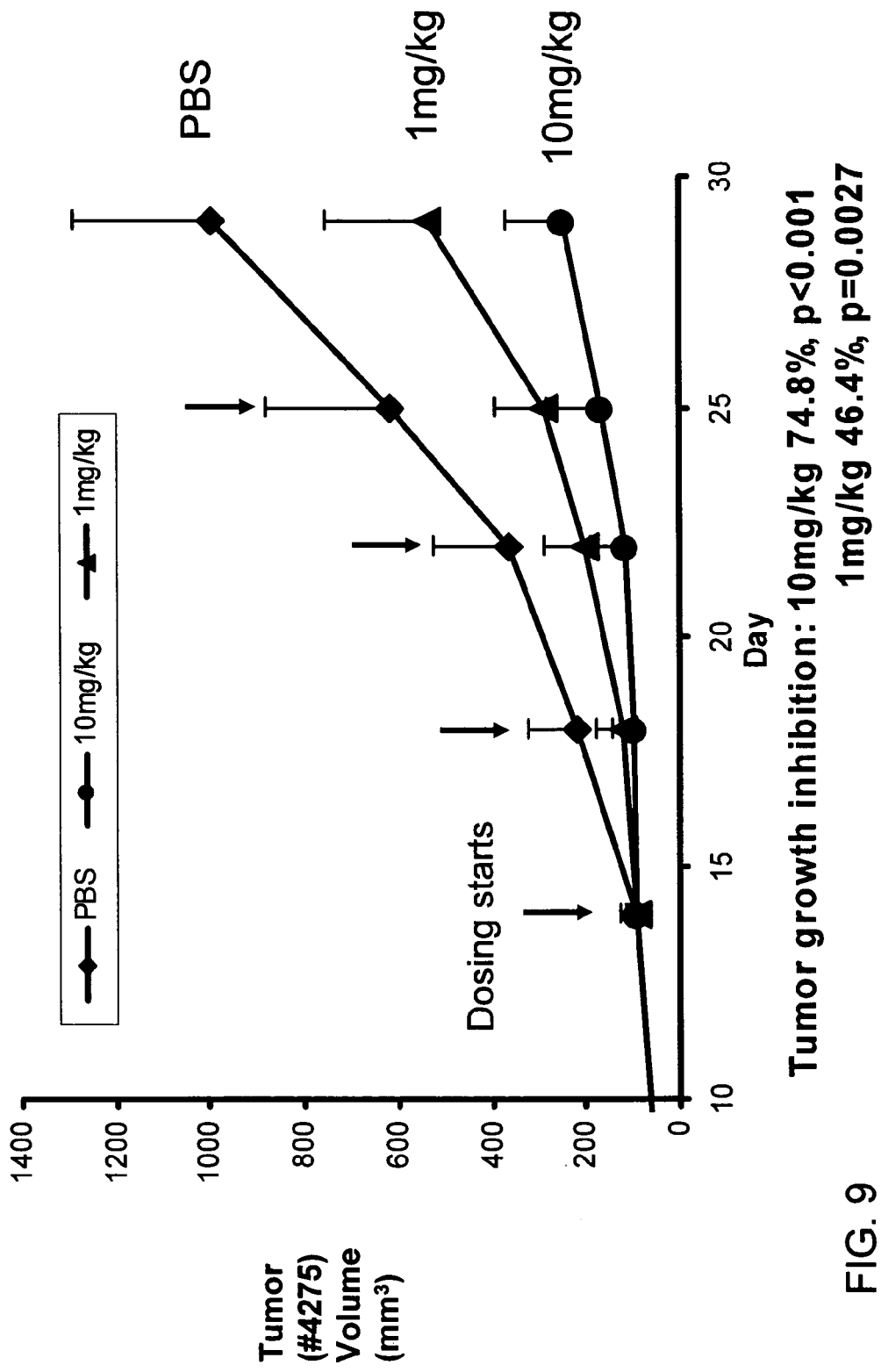
FIG. 9 is a graph summarizing data on the effect of anti-HGF antibody (mAb294) on the growth of the breast Her2 derived MET/HGF complemented tumor 4275. Anti-HGF antibody (mAb294) was injected at either 10 mg/kg or 1 mg/kg intraperitoneally into breast Her2 derived MET/HGF complemented tumor 4275 twice a week. The effect of the antibody treatment on tumor volume was measured over 30 days. PBS was used as a control.

Tumor growth inhibition was tested by using a monoclonal antibody against human HGF mAb294 (R&D Systems). Tumors were established by subcutaneous inoculation of dissociated HGF/MET tumors (4272 and 4275) into NCR female nude mice. When tumors grew to 50-100 mm$^3$, the animals were randomized into three groups. One group received vehicle (PBS) and the other two received 1 or 10 mg/kg of mAb294 by i.p. injection twice a week. Tumor size was determined by caliper measurement and calculated by the equation of (long diameter×short diameter$^2$)/2, twice weekly. The experiment was terminated 3 days after the 4$^{th}$ dose. In tumor 4272, 1 mg/kg inhibited tumor growth by 49.7% (p=0.08) and 10 mg/kg inhibited tumor growth by 89.9% (p=0.0034). In tumor 4275, 1 mg/kg inhibited tumor growth by 46.4% (p=0.027) and 10 mg/kg inhibited tumor growth by 74.8% (p<0.001) (FIGS. 8 and 9).

Other embodiments are within the following claims.

The invention claimed is:

1. A method of producing primary tumor material, the tumorigenicity of which depends on a recombinant human gene of interest, comprising the steps of:
   (a) providing a conditionally tumorigenic mouse cell comprising
      (i) one or more mutations such that both alleles of an endogenous tumor suppressor gene are absent or non-functional, and
      (ii) a recombinant oncogene operably linked to an inducible promoter, wherein
         (1) tumorigenicity of the conditionally tumorigenic mouse cell is dependent upon expression of the inducible recombinant oncogene, and
         (2) the inducible promoter is in the uninduced state; and
   (b) introducing into the cell a recombinant human gene of interest that functionally complements the recombinant oncogene;
   (c) introducing the cell of step (b) into an immunocompromised recipient mouse;
   (d) maintaining the recipient mouse for a suitable tumor latency period, in the absence of an inducer of the inducible promoter; and
   (e) harvesting primary tumor material from the directed complementation tumor.

2. The method of claim 1, wherein the tumor suppressor gene is selected from the group consisting of Rb, P53, INK4a, PTEN, LATS, Apaf1, Caspase 8, APC, DPC4, KLF6, GSTP1, ELAC2/HPC2, NKX3.1, ATM, CHK2, ATR, BRCA1, BRCA2, MSH2, MSH6, PMS2, Ku70, Ku80, DNA/PK, XRCC4, Neurofibromatosis Type 1, Neurofibromatosis Type 2, Adenomatous Polyposis Coli, the Wilms tumor-suppressor protein, Patched and FHIT.

3. The method of claim 2, wherein the tumor suppressor gene is selected from the group consisting of INK4a, P53, PTEN and Rb.

4. The method of claim 3, wherein the tumor suppressor gene is INK4a.

5. The method of claim 1, wherein the recombinant oncogene is selected from the group consisting of Her2, KRAS, HRAS, NRAS, EGFR, MDM2, TGF-β, RhoC, AKT, c-myc, β-catenin, PDGF, C-MET, PI3K-CA, CDK4, cyclin B1, cyclin D1, estrogen receptor alpha gene, progesterone receptor gene, ErbB1, ErbB3, PLK3, KIRREL, ErbB4, TGFα, ras-GAP, Shc, Nck, Src, Yes, Fyn, Wnt, Bcl2, PyV MT antigen, and SV40 T antigen.

6. The method of claim 5, wherein the recombinant oncogene is selected from the group consisting of Her2, C-MET, PI3K-CA, KRAS and AKT.

7. The method of claim 6, wherein the recombinant oncogene is Her2 or KRAS.

8. The method of claim 1, wherein the gene of interest is selected from the group consisting human AKT1, activated form of human EGFR, human mTOR, human cMET and human HGF.

9. The method of claim 1, wherein the inducible promoter system is selected from the group consisting of a tetracycline-dependent promoter regulatory system, a metallothionine promoter system, an IPTG/lacI promoter system, an ecdysone promoter system, and a Gal4/UAS system.

10. A method of testing a compound for anti-tumor effects, comprising:
   (a) producing, according to claim 1, primary tumor material, the tumorigenicity of which depends on expression of a recombinant human gene of interest;
   (b) implanting the primary tumor material into a multiplicity of host mice;
   (c) obtaining tumors in the mice derived from the implanted cells;
   (d) administering suitable amounts of a test compound to the mice; and
   (e) determining anti-tumor effects, if any, of the test compound.

11. The method of claim 10, wherein the compound tested is an antibody.

12. The method of claim 10, wherein the human gene of interest is a human MET gene or a human HGF gene.

* * * * *